(12) United States Patent
Tanner et al.

(10) Patent No.: US 6,305,541 B1
(45) Date of Patent: Oct. 23, 2001

(54) CARTRIDGE ASSEMBLY PACKAGING

(76) Inventors: John C. Tanner, 115 E. Witchwood La., Lake Bluff, IL (US) 60044; Mark Ward, 863 Waterfort Dr., Grayslake, IL (US) 60030; James G. Freund, 1036 S. River Rd., Des Plaines, IL (US) 60016; Joseph D. Lokay, 1450 Homestead Pl.; Harley E. Vasper, Jr., 1489 Janasu Rd., both of McPherson, KS (US) 67460; Julian L. Carrington, III, 213 Stafford Dr., Mundelein, IL (US) 60064; Darlene Cronin, 3127 23$^{rd}$ St., Zion, IL (US) 60099; James P. Perry, 1010 92$^{nd}$ St., Pleasant Prairie, WI (US) 53158

( * ) Notice: Subject to any disclaimer, the term of this patent is extended or adjusted under 35 U.S.C. 154(b) by 0 days.

(21) Appl. No.: 09/396,719

(22) Filed: Sep. 15, 1999

(51) Int. Cl.$^7$ ..................................... B65D 83/10
(52) U.S. Cl. ....................... 206/366; 206/459.5; 206/807; 206/497
(58) Field of Search ..................................... 206/364, 365, 206/366, 372, 459.5, 807, 497; 220/610, 617, 620

(56) References Cited

U.S. PATENT DOCUMENTS

| 3,074,542 | * | 1/1963 | Myerson et al. ...................... 206/366 |
| 4,303,190 | * | 12/1981 | Ditto et al. ............................ 220/620 |
| 4,377,234 | * | 3/1983 | Kaplan ................................... 206/497 |
| 4,585,445 | | 4/1986 | Hadtke . |
| 4,781,697 | * | 11/1988 | Slaughter ............................... 604/192 |
| 4,836,400 | * | 6/1989 | Chaffey et al. ........................ 220/617 |
| 4,892,525 | * | 1/1990 | Hermann, Jr. et al. ............... 206/365 |
| 4,931,043 | | 6/1990 | Ray et al. . |
| 4,935,014 | | 6/1990 | Haber . |
| 5,048,708 | * | 9/1991 | Musco ................................... 206/428 |
| 5,385,105 | * | 1/1995 | Withers, Jr. et al. ................. 206/366 |
| 5,544,770 | * | 8/1996 | Travisano .............................. 206/807 |
| 5,605,230 | * | 2/1997 | Marino, Jr. et al. .................. 206/534 |
| 5,730,729 | | 3/1998 | Bergstresser et al. . |
| 6,032,823 | * | 3/2000 | Bacon ................................... 220/620 |

OTHER PUBLICATIONS

Flex Products, Carlstadt, NJ—Product Brochure, prior to Sep. 15, 1999.

* cited by examiner

*Primary Examiner*—Paul T. Sewell
*Assistant Examiner*—Shian Luong
(74) *Attorney, Agent, or Firm*—Brian R. Woodworth

(57) ABSTRACT

A combination of a package and a cartridge filled with a medicament. The package includes a tube having first and second ends and a cylindrical wall. The package further includes a plug disposed within the tube proximate the first end. A removable cover covers the first end of the tube. The cartridge is disposed within the package. The cartridge has a cylindrical wall defining an interior space. A grommet is disposed within the interior space and a septum is disposed on a first end portion of the cylindrical wall. A medicament is disposed within the cylindrical wall between the grommet and the septum.

13 Claims, 4 Drawing Sheets

CARTRIDGE ASSEMBLY PACKAGING

BACKGROUND OF THE INVENTION

1. Field of the Invention

This invention relates to the packaging for a cartridge assembly.

2. Description of the Prior Art

Medicament containing cartridges are well known in the art and are in widespread commercial use. One such cartridge conventionally includes a cylindrical glass body (wall) closed at the distal end with a flexible plunger (grommet) slidable within the bore of the cartridge and closed at the proximal end with a septum secured to the cartridge by a crimped-on collar. The grommet is typically positioned within the cartridge so that the glass wall extends below the grommet. The necked down proximal end conventionally is fitted with a needle hub assembly. One such cartridge is described in U.S. Pat. No. 5,730,729. This patent is incorporated herein by reference. The needle-hub assembly and cartridges are described collectively as a "cartridge assembly." The details of the application of the cartridge assemblies are not pertinent to this discussion and therefore will not be described here. Suffice it to say, the cartridge assemblies are typically used in a hospital and are assembled as a syringe to dispense medicament. The cartridges are filled with medicament before they are made commercially available.

There are many types of medicaments that are commercially available in a cartridge. Some of those medicaments have been designated by the government as controlled substances. That is, access to such substances is limited to medical personnel having proper authorization. Controlled substances such as morphine are often the subject of theft. The criminal act may entail actually stealing the cartridges outright or more frequently, may entail inserting a needle in the grommet in the distal end of the cartridge to withdraw the controlled substance. The thief may even replace the controlled substance with water. In this respect, the puncture may cause contamination and may go undetected for some time.

Cartridge assemblies today are packaged in different forms. One such form is shown in FIGS. 1 and 1A. The packaging is currently marketed by Abbott Laboratories under the trademark Detecto Seals®. The cartridge assemblies 12 are bundled in plastic packaging 10 in a linear or side-by-side spaced relationship. The packaging 10 includes a metal tray 14 at the bottom thereof for receiving the distal ends of the cartridge assemblies 12. The metal tray 14 serves to prevent a thief from inserting a needle through the bottom of the packaging 10 and into a grommet of an individual cartridge assembly 12, in an attempt to withdraw the controlled substance.

Although this type of packaging has been useful, it has its disadvantages. First, in order to gain access to an individual cartridge assembly 20, the authorized medical professional must bend the top portion 16 of the packaging 10 so that the portion tears along the serrated edge 18. See FIG. 1A. However, quite often the medical professional inadvertantly tears further along the serrated edge 18 which exposes the adjacent cartridge assembly 22. Once that area is open the exposed cartridges must be discarded to protect against contamination and/or possible tampering. This loss in supply becomes quite costly. Further, the shape of the packaging is disadvantageous for its use in the hospital. Automated dispensing machines (ADM) are used in the hospitals to dispense the cartridge assemblies prefilled with controlled substances. In one such machine made by Pyxis, Inc. of San Diego, Calif., the drawers are not large enough to receive the package shown in FIG. 1.

Another form of packaging used today is a cardboard rectangular container designed to enclose an individual cartridge assembly. This type of packaging also has its disadvantages. First, the cardboard does not provide any protection against withdrawing the controlled drug via a needle through packaging and through the grommet of the cartridge assembly. Further, in other automated dispensing machines such as those made by Diebold, Inc. of North Canton, Ohio, cartridges may be dispensed individually, one at a time, by a module which allows such cartridges to roll down a smooth path toward the medical professional. However, the rectangular cardboard container cannot be used because it cannot roll.

It would be desirable to provide a packaging for a cartridge assembly that would avoid the disadvantages of the prior art described above.

SUMMARY OF THE INVENTION

There is provided a package for enclosing a cartridge assembly including a cartridge pre-filled with medicament. In one embodiment, the package includes (1) a tube having a first open end, a second closed end and a cylindrical wall defining a hollow interior chamber in communication with said ends for receiving said cartridge assembly, (2) a cover for covering said first open end of said tube; and (3) a first structure for securing said cover to said tube.

In accordance with another aspect of the invention, there is provided a package for enclosing a cartridge assembly including a cartridge pre-filled with medicament. The package includes a tube having a first open end, a second closed end and a hollow interior chamber in communication with said ends for receiving said cartridge assembly; a cover for covering said first open end of said tube; a first structure for securing said cover to said tube; and a second structure for protecting against access to the medicament in the cartridge assembly adjacent said second closed end.

In accordance with yet another aspect of the invention, there is provided an assembly of individually packaged cartridge assemblies. The assembly includes a plurality of cartridge assemblies, each assembly including a cartridge pre-filled with medicament; an individual package enclosing each of said cartridge assemblies; and a combining structure for combining said individually packaged cartridge assemblies together as a unit. The individual packages each include: a tube having a first open end, a second closed end, and a hollow interior chamber in communication with said ends for receiving said cartridge assembly; a cover for covering each of said first open end of said tubes; and a label for securing said cover to said tube.

Other advantages will become readily apparent upon references to the following description of the preferred embodiments when read in light of the accompanying drawings.

DESCRIPTION OF THE PREFERRED EMBODIMENT

Figure 1:
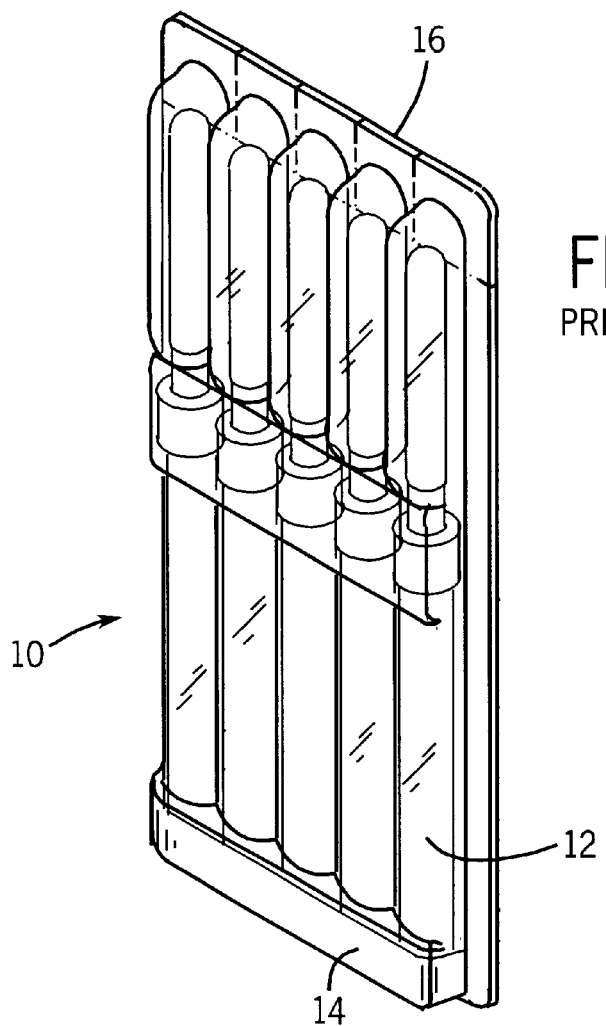
FIG. 1 is a perspective view of the prior art packaging for a plurality of cartridge assemblies.
Figure 1A:
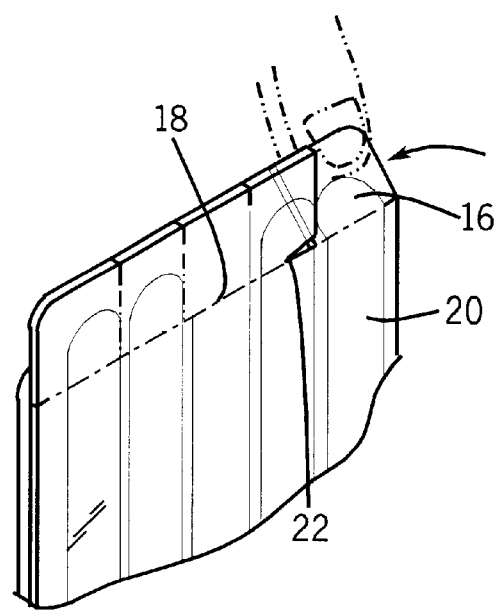
FIG. 1A is a top view of the packaging shown in FIG. 1.

The packaging of the present invention is depicted in FIGS. 2–11. In such Figures there is shown a package (or packaging) 40 for housing a cartridge assembly 42. The cartridge assembly 42 includes a cartridge 44 including a cylindrical transparent wall made of glass, a flexible grommet at the distal end 42a of the cartridge 44 which is capable of sliding within the bore of the cartridge 44 and a closed proximal end 42b with a septum secured to the cartridge by a crimped-on collar (not shown). For purposes of this discussion, the cartridge assembly 42 also includes the needle hub assembly 46 attached, in addition to the glass cartridge 44. However, the packaging of the present invention may be designed to enclose an individual cartridge by itself. In this configuration, the needle hub assembly can be installed on the cartridge 44 after it has been removed from the packaging 40.

Figure 2:
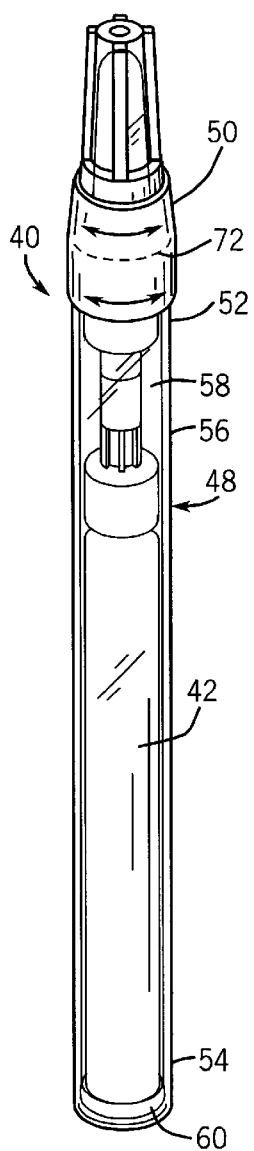
FIG. 2 is perspective view of packaging for a single cartridge assembly according to the present invention.
Figure 3:
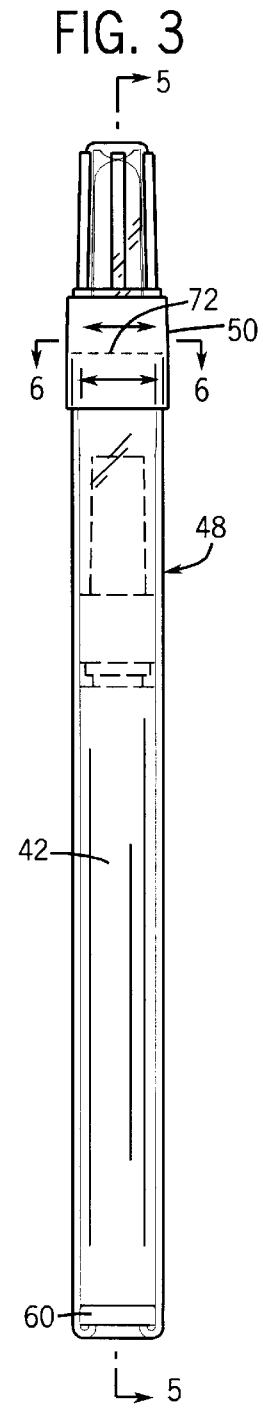
FIG. 3 is a side view of the packaging shown in FIG. 2.
Figure 4:
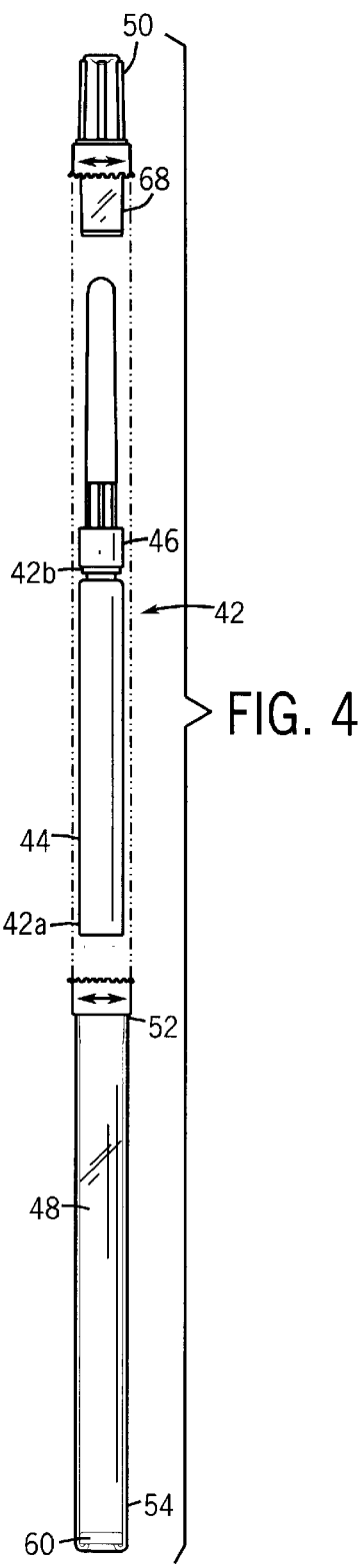
FIG. 4 is an exploded view of the packaging and cartridge assembly shown in FIG. 2.
Figure 5:
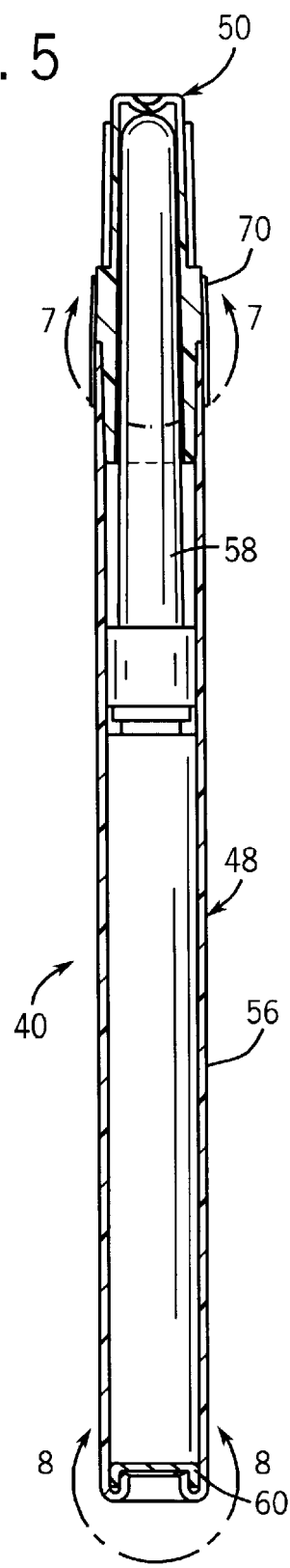
FIG. 5 is a cross-sectional view of the packaging shown in FIG. 3 along lines 5—5.
Figure 6:
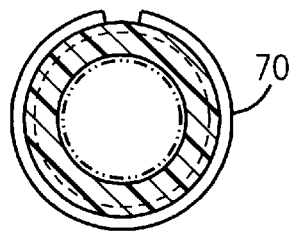
FIG. 6 is a cross-sectional view of the packaging shown in FIG. 3 along the lines 6—6.
Figure 7:
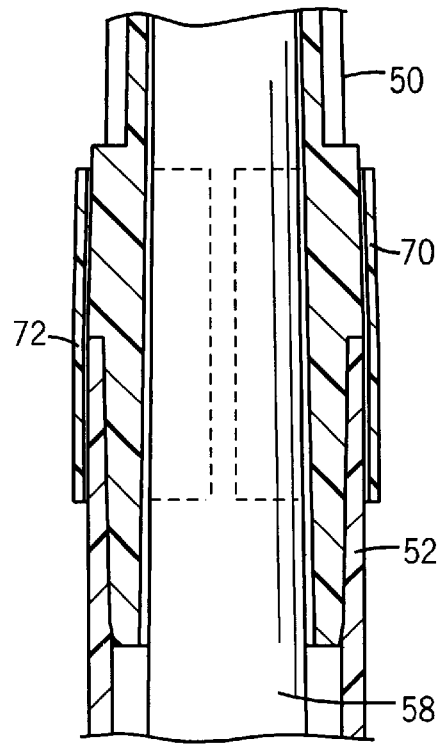
FIG. 7 is a sectional view of the packaging shown in FIG. 5 along the rotational lines 7—7.

As best seen in FIGS. 2 and 3, the cartridge assembly 42 is situated within the packaging 40. The packaging 40 includes a tube 48 which has a first open end 52 and a second end 54. The tube 48 is preferably made of plastic which is transparent. However, the tube 48 could be any color desired. (Color tubes may be necessary for cartridges filled with medicaments which are light sensitive.) The tube 48 has a cylindrical wall 56 which defines a hollow interior chamber 58 in communication with the first and second ends 52, 54 for receiving the cartridge assembly 42.

Package 40 includes an aluminum plug 60 is positioned within the interior chamber 58 adjacent the second end 54 for closing second end 54 from an external environment of tube 48, and, more importantly, for protecting against access to the contents of the cartridge 42 through second closed end 54 by a needle/syringe assembly. Any puncture through the cylindrical wall 56 of the tube 48 would not gain access to drug. The needle would be met by a hard glass surface of the cartridge 44.

Figure 8:
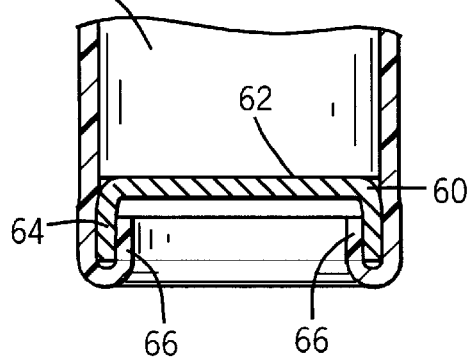
FIG. 8 is sectional view of the packaging shown in FIG. 5 along the rotational line 8—8.

As best seen in the embodiment of the present invention depicted in FIG. 8, the plug 60 includes a top wall 62 and an annular side wall 64 extending from the top wall 62. The surface of the top wall faces the interior chamber 58 of the tube 48 and the annular wall 64 extends downwardly toward the second end 54 of the tube 48. The outer surface of the annular wall 64 is fit snugly against the inside surface of the cylindrical wall which defines the interior hollow chamber 58 of the tube 48. The tube 48 has a portion 66 (of the wall) bent inwardly toward the plug 60. Portion 66 then extends around annular wall 64 of plug 60 as depicted in FIG. 8, the bent portion 66 is bent around the annular wall 64 such that part of bent portion 66 extends in a direction parallel to the cylindrical wall 56. However, the bent portion 66 can be at other angles with respect to the cylindrical wall so long as it prevents the plug 60 from being removed through the second end 54. As shown, the bent portion 66 does not actually meet the bottom surface of the top wall 62.

Figure 12:
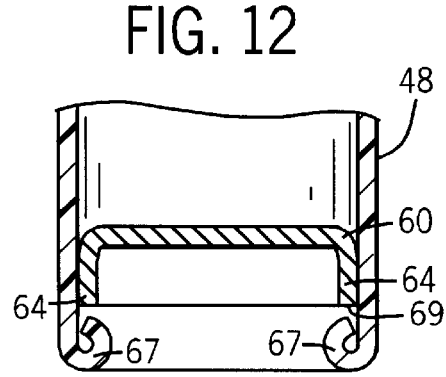
FIG. 12 is a cross-sectional view of an alternative embodiment of the packaging in accordance with the present invention.

FIG. 12 illustrates an alternative embodiment of the packaging of the present invention. Similar to the embodiment described above, a bent portion 67 is curled inwardly toward the bottom of plug 60. In this embodiment however, the bent portion 67 does not actually touch the ledge 69 of the annular wall 64 of the plug 60. However, the plug 60 (at the ledge 69) may in fact rest on the bent portion 67 when the cartridge assembly is stored within the tube 48.

Note that the plug 60 is preferably made of aluminum. However, any metal, plastic, or other material can be used that is sufficiently strong to prevent a needle from penetrating therethrough to withdraw the contents of the cartridge 44.

Figure 10:
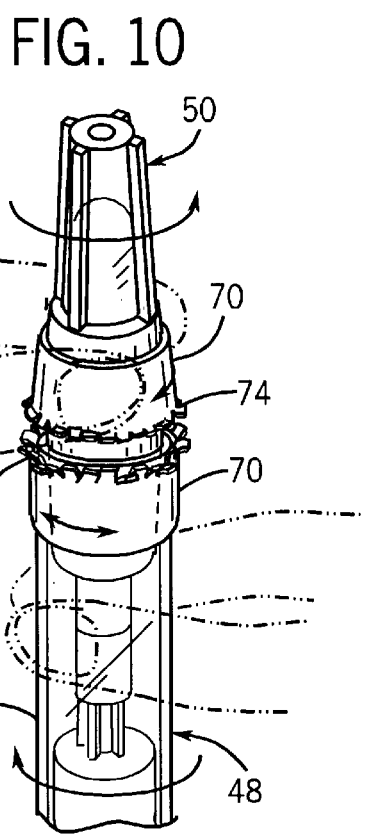
FIG. 10 is view of the top of the packaging and cover showing the tamper evidence feature.

The packaging 40 also includes a cover 50 or cap for covering the open first end 52 of the tube 48. The cover 50 is preferably made of clear plastic. The cover 50 is cylindrically shaped and sized to cover the tube 48. The cover 50 has a portion 68 that has a smaller diameter than the tube 48 to enable the portion 68 to fit within the interior chamber 58 of the tube 48. The package 40 also has a structure for securing the cover 50 to the tube 48. The securing structure is preferably a label 70 which includes a tamper evidence indication element. This element is a serrated edge 72 or perforated edge. In operation, the medical personnel twists the cover 50 as shown in FIG. 10 with respect to tube 48, thereby causing the label to tear along the serrated edge 72 to form a plurality of paper pieces 74. These paper pieces 74 provide the indication of tampering with the contents of the packaging at the first end of the tube 48. In FIG. 10, the cover is twisted in a counterclockwise direction, however, the cover 50 can be twisted in either direction.

Figure 9:
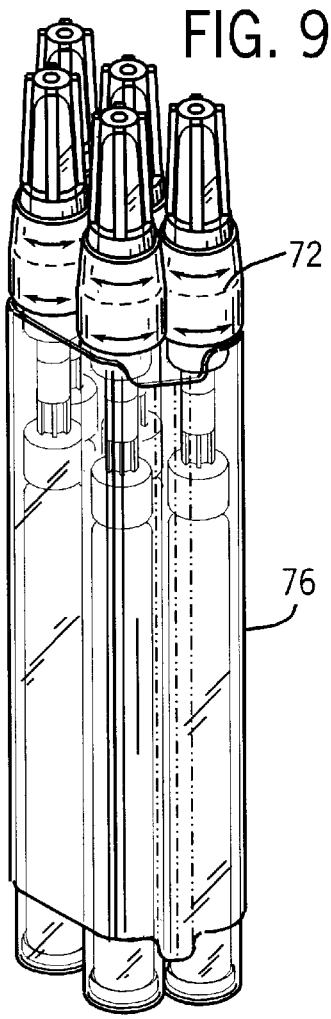
FIG. 9 is perspective view a bundle of individual packaging for a five cartridge assemblies.
Figure 11:
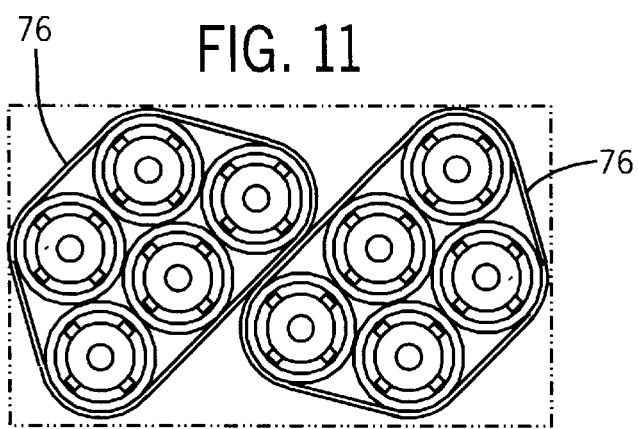
FIG. 11 is a plan view of two five packs of cartridge assemblies.

FIGS. 9 and 11 illustrate a pack of five individually packaged cartridge assemblies. The assemblies are held together by a combining structure which preferably is a shrink wrap 76, as shown in FIGS. 9 and 11. The combined cartridge assemblies are in the shape of a partial pyramid. This shape is important because it allows the pack in certain automated dispensing machines. The shrink wrap 76 can be easily removed to access the individual packaged cartridge assemblies. The user must simply pull on a tear strip to remove the shrink wrap 76. However, there are other designs for tearing the shrink wrap. FIG. 11 illustrates two sets of five packs combined together.

With the present packaging, the following advantages are found. First, tamper indication is provided for individual packages. Second, the individual cartridge assembly can be dispensed individually with protection. Third, the packaging can "roll" in an automated dispensing machine for dispensing to the authorized medical personnel. Fourth, the medical personnel can see through the clear plastic to determine breakage and tamper indication. Fifth, the packaging allows for unused individual cartridge assemblies to be inspected and returned to the pharmacy for reshelving instead of being recounted and destroyed.

The invention has been described in detail with particular reference to certain preferred embodiments thereof, but it will be understood that variations and modifications can be effected within the spirit and scope of the invention.

What is claimed is:

1. An assembly of individually packaged cartridges, said assembly comprising:
   a plurality of individual packages, each of said plurality of individual packages constructed to enclose a cartridge;
   a plurality of cartridges, one of said plurality of cartridges disposed within each of said plurality of individual packages; and
   a combining package for combining said plurality of individual packages together as a single unit;
   each of said plurality of individual packages including:
      a tube having a first end, a second end, and a cylindrical wall defining a hollow interior chamber in communication with said first and second ends;
      a plug disposed within said hollow interior chamber proximate said second end, said plug constructed to prevent access to a cartridge disposed within said hollow interior chamber through said second end of said tube;
      a cover for covering said first end of said tubes; and
      a securing structure for securing said cover to said tube.

2. The assembly of claim 1 wherein said combining structure is shrink wrap.

3. The assembly of claim 1 wherein said securing structure is a label with a tamper indication element for indicating whether a person has attempted to access the contents of the tube adjacent the first open end of the tube.

4. The assembly of claim 1 wherein each said plug has a top wall and an annular side wall extending from said top wall.

5. The assembly of claim 4 wherein each said tube has a portion which is bent around said annular wall in a direction toward the interior chamber of said tube.

6. The assembly of claim 5 wherein said portion which is bent includes a section that is substantially parallel to said cylindrical wall.

7. A method for storing a medicament, said method comprising:
   providing a cartridge having a cylindrical wall having a first end portion and a second end portion, said cylindrical wall defining an interior space, a grommet disposed within said interior space defined by said cylindrical wall proximate said second end portion, and a septum disposed on said first end portion of said cylindrical wall, a medicament being disposed within said interior space defined by said cylindrical wall between said grommet and said septum;
   providing a package for said cartridge containing said medicament, said package comprising:
      a tube having a first end, a second end, and a wall defining a hollow interior chamber in communication with said first and second ends;
      a plug disposed within said hollow interior chamber proximate said second end, said plug constructed to prevent access by a hypodermic needle to a cartridge disposed within said hollow interior chamber through said second end of said tube when said plug is disposed within said hollow interior chamber; and
      a removable cover constructed to cover said first end of said tube;
   placing said cartridge containing said medicament within said hollow interior chamber of said tube; and
   placing said cap on said first end of said tube.

8. A method in accordance with claim 7, wherein said plug has a top wall and an annular side wall extending from said top wall, and wherein said wall of said tube has a portion constructed to retain said plug within said tube.

9. A method in accordance with claim 7, wherein said method further comprises providing a securing structure for securing said cover to said tube, and placing said securing structure on said package.

10. A method in accordance with claim 7, wherein said package further comprises a tamper evidence seal mounted on said tube and said cap.

11. A combination comprising:
   a package comprising:
      a tube having a first end, a second end, and a wall defining a hollow interior chamber in communication with said first and second ends;
      a plug disposed within said hollow interior chamber proximate said second end, said plug constructed to prevent access by a hypodermic needle to a cartridge disposed within said hollow interior chamber through said second end of said tube when said plug is disposed within said hollow interior chamber; and
      a removable cover for covering said first end of said tube; and
   a cartridge disposed within said hollow interior chamber of said package, said cartridge having a cylindrical wall having a first end portion and a second end portion, said cylindrical wall defining an interior space, a grommet disposed within said interior space defined by said cylindrical wall proximate said second end portion, and a septum disposed on said first end portion of said cylindrical wall, a medicament being disposed within said interior space defined by said cylindrical wall between said grommet and said septum.

12. A combination in accordance with claim 11, wherein said package further comprises a tamper evident seal mounted on said tube and said cap.

13. A combination comprising:
   a package comprising:
      a tube having a first end, a second end, and a wall defining a hollow interior chamber in communication with said first and second ends, an end wall disposed on said second end, said end wall separating said hollow interior from an external environment of said tube, said end wall constructed to prevent access by a hypodermic needle to a cartridge disposed within said hollow interior chamber through said second end of said tube; and
      a removable cover for covering said first end of said tube; and
   a cartridge disposed within said hollow interior chamber of said package, said cartridge having a cylindrical wall having a first end portion and a second end portion, said cylindrical wall defining an interior space, a grommet disposed within said interior space defined by said cylindrical wall proximate said second end portion, and a septum disposed on said first end portion of said cylindrical wall, a medicament being disposed within said interior space defined by said cylindrical wall between said grommet and said septum.

* * * * *